United States Patent [19]

Mazanec et al.

[11] Patent Number: 4,705,532
[45] Date of Patent: Nov. 10, 1987

[54] ALCOHOL COMPOSITIONS FOR BLENDING WITH GASOLINE

[75] Inventors: Terry J. Mazanec; John G. Frye, Jr., both of Solon; Harley F. Hardman, Lyndhurst, all of Ohio

[73] Assignee: The Standard Oil Company, Cleveland, Ohio

[21] Appl. No.: 9,105

[22] Filed: Jan. 30, 1987

Related U.S. Application Data

[63] Continuation of Ser. No. 754,880, Jul. 15, 1985, abandoned.

[51] Int. Cl.$^4$ .............................................. C10L 1/02
[52] U.S. Cl. ........................................... 44/53; 44/56; 44/77; 518/713
[58] Field of Search ................. 44/56, 53, 77; 518/713

[56] References Cited

U.S. PATENT DOCUMENTS

| | | | |
|---|---|---|---|
| 2,591,672 | 4/1952 | Catteral | 44/56 |
| 2,787,628 | 4/1957 | Himmler et al. | 518/714 |
| 3,832,149 | 8/1974 | Kozlowski et al. | 44/56 |
| 3,901,664 | 8/1975 | Kozlowski et al. | 44/56 |
| 4,298,354 | 11/1981 | Hardman et al. | 44/56 |
| 4,460,378 | 7/1984 | Di Pietro et al. | 44/54 |
| 4,469,903 | 9/1984 | Schmidt | 568/918 |
| 4,540,713 | 9/1985 | Hardman et al. | 518/713 |

FOREIGN PATENT DOCUMENTS

| | | |
|---|---|---|
| 0608361 | 1/1935 | Fed. Rep. of Germany. |
| 2083469A | of 1915 | United Kingdom .................... 29/15 |
| 0229715 | 2/1925 | United Kingdom. |

*Primary Examiner*—William R. Dixon, Jr.
*Assistant Examiner*—Margaret B. Medley
*Attorney, Agent, or Firm*—Larry W. Evans; David J. Untener; Raymond F. Keller

[57] ABSTRACT

An alcohol composition suitable for mixing with gasoline comprises at least 30 percent by weight of methanol, the remainder of said composition comprising higher alcohols the distribution of which on a methanol-free basis is $C_2$—about 10 to 90 weight percent,
$C_3$—about 15 to 60 weight percent,
$C_4$—about 0.5 to 35 weight percent,
$C_5$—about 0 to 15 weight percent,
$C_6$—about 0 to 15 weight percent, and wherein the percent of $C_3$ is equal to or greater than 1.25 times the percent of $C_4$.

The alcohol composition can be prepared from hydrogen and carbon monoxide under alcohol forming conditions in the presence of a catalyst containing copper and uranium and alkali or alkaline earth metal.

14 Claims, No Drawings

ALCOHOL COMPOSITIONS FOR BLENDING WITH GASOLINE

This is a continuation of co-pending application Ser. No. 754,880 filed on July 15, 1985 abandoned.

BACKGROUND OF THE INVENTION

This invention relates to a new alcohol composition suitable for mixing with gasoline, to a gasoline composition containing same and to a process for its preparation.

It is well known to incorporate methanol into gasoline for the purpose of increasing the amount of useful fuel. Unfortunately, the presence of a small amount of water in a methanol/gasoline mixture causes separation of the methanol and gasoline phases. In order to overcome this problem, higher alcohols have been added to methanol/gasoline mixtures, and the compositions so obtained are able to tolerate a much greater amount of water than a simple methanol/gasoline mixture.

U.S. Pat. No. 4,298,354 describes an alcohol composition for mixing with gasoline comprising at least 40 percent of methanol, the remainder of said composition comprising higher alcohols, the distribution of which on a methanol-free basis is $C_2$—4 to 25 weight percent,
$C_3$—0.1 to 25 weight percent preferably 9 to 25 percent,
$C_4$—0.5 to 70 weight percent preferably 40 to 70 percent,
$C_5$—0.1 to 12 weight percent,
$C_6$—0.1 to 10 weight percent.

This patent further discloses a modified gasoline composition containing a homogeneous solution of gasoline and a composition of the above alcohols. This patent further discloses a process for the preparation of the above described alcohol composition which process comprises contacting carbon monoxide and hydrogen with an oxide complex catalyst of formula

$$Cu_aThM_bA_cO_x$$

wherein M is one or more of Ca, Mo, Rh, Mn, Pt, Ce, Cr, Zn, Al, Ti, La, V, U, Ru, Re and Pd and
a is 0.5 to 2.5,
b is 0.01 to 1.0,
c is 0.05 to 0.9 and
x is a number such that the valence requirements of the other elements for oxygen is satisfied.

Further, Great Britain Patent Application No. 2 083 469A describes an alcohol composition containing the following
$C_1$—35 to 75 percent
$C_2$—2 to 5 percent (2.9 to 21.9 percent)
$C_3$—3 to 12 percent (4.8 to 41.4 percent)
$C_4$—10 to 30 percent (19.2 to 75 percent)
$C_{4+}$—5 to 25 percent (9.6 to 62.5 percent)
The figures in brackets are on a methanol-free basis.

For gasoline blending it is desirable that an alcohol composition contains alcohols of carbon number high than $C_1$ in order to achieve good cloud point properties. However, when considered from its production from syn gas it is desirable that alcohols of carbon number 4 and higher do not form a significant proportion of the product, since for each molecule of carbon monoxide used in building the carbon chain, an atom of oxygen must be discarded either in the form of water or carbon dioxide with consequent loss of feed. It is desirable to obtain an alcohol composition containing alcohols of carbon number at least 2 but in which the proportion of alcohols of carbon number 3 is high in relation to the higher carbon number alcohols.

It is therefore an object of the present invention to provide a new alcohol composition suitable for mixing with gasoline in which the percent by weight of $C_3$ alcohols is at least 1.25 times that of the $C_4$ alcohols and in addition a gasoline modified by the incorporation of this new alcohol composition.

SUMMARY OF THE INVENTION

According to the present invention, there is provided an alcohol composition suitable for mixing with gasoline comprising at least 30 percent by weight of methanol, the remainder of said composition comprising higher alcohols the distribution of which on a methanol-free basis is $C_2$—about 10 to 90 weight percent
$C_3$—about 15 to 60 weight percent
$C_4$—about 0.5 to 35 weight percent
$C_5$—about 0 to 15 weight percent
$C_6$—about 0 to 15 weight percent and wherein the percent of $C_3$ is at least 1.25 times the percent of $C_4$.

The alcohol composition of the present invention is distinguished from those disclosed in U.S. Pat. No. 4,298,354 and Great Britain Application No. 2 083 469A referred to above in that the ratio of the percent of $C_3$ to $C_4$ is at least 1.25:1.

In addition, the present invention further provides an alcohol/gasoline mixture comprising a homogeneous solution of gasoline and the alcohol composition of the present invention.

The alcohol composition of the present invention can be prepared by the reaction of carbon monoxide and hydrogen in the presence of a catalyst composition containing alkali metal or alkaline earth metal uranate of the formula $Cu_aUM_bA_cO_x$ where M is one or more metals selected from the group consisting of Th, Pd, Mn, Cr, Fe, Co, Zn, Ce, V, Ru, Al, Re, Os, Pt, Ir, Ag, Ti, La and Zr, A is an alkali or alkaline earth metal or mixture thereof and a is from 0.01 to 5.0;
b is from 0 to 5.0 with the proviso that when M is Th the value of b is less than 1;
c is a number up to 5.0 selected so that the catalyst contains more than 2 percent by weight of Metal A;
x is a number such that the valence requirements of the other elements for oxygen are satisfied.

In stating that the valence requirements of the other elements for oxygen are satisfied, we do not intend to exclude catalysts where copper is present in an elemental or zerovalent state, provided there is some chemically bound oxygen in the catalyst.

The above formula is not intended to be limited to catalysts containing only the elements specified for M and A in combination with copper, but includes the optional presence of other elements in addition to those specified.

The catalysts employed in the present invention are distinguished from those disclosed in U.S. Pat. No. 4,298,354 referred to above in that they contain alkali metal or alkaline earth metal uranate. Further, when thorium is present, the atomic ratio of U to Th is always greater than 1. This difference in composition enables the catalyst to produce a higher proportion of $C_3$ to $C_4$ alcohols than is disclosed in U.S. Pat. No. 4,298,354.

DETAILED DESCRIPTION OF THE INVENTION

As stated above, the catalyst composition contains more than 2 percent by weight of the metal A. Preferably, the catalyst composition contains at least 5 percent by weight of the metal A. Although there is no upper limit, it is not convenient to exceed 20 or 15 percent by weight. Also as stated above, when thorium is present the atomic ratio of U to Th is greater than 1. Preferably, this ratio is greater than 2.

Preferred ranges for a, b and c in the above formula are from 0.5 to 2.5, 0 to 0.5 and 0.5 to 2.0, respectively. The catalyst composition will, in many cases, contain at least 50 percent by weight of uranium.

The catalyst composition may be prepared by mixing compounds of the metals in solution and precipitating the metals from solution (by the addition of a precipitating agent) in the form of their oxides or a form thermally decomposable to their oxides. A method similar to that described in U.S. Pat. No. 4,298,354 may be employed, except that in the present case a soluble compound of uranium is employed.

The technique described in U.S. Pat. No. 4,298,354 involves precipitation from an aqueous solution and while this is generally very satisfactory for most metals is has been found that certain uranium compounds have a high solubility in water, even at pH values above 9, and uranium is for this reason not always easily precipitated with the other metals.

It is therefore preferred to precipitate the metals from a polar organic solvent.

The polar organic solvent can be a ketone such as acetone, an ester such as methyl acetate, an ether such as tetrahydrofuran or an alcohol such as ethanol.

The precipitation of the metals from the solution in the polar organic solvent is conveniently effected by mixing the solution with a solution of the precipitating agent also in a polar organic solvent.

The term polar organic solvent as used herein is intended to mean a solvent containing at least 50 percent by volume of a polar organic solvent. Water can be present but desirably comprises less than 40 percent by volume of the total and preferably less than 10 percent. Preferably, the solvent consists essentially of the polar organic solvent which is preferably an alcohol or mixture of alcohols.

Preferred alcohols are $C_1$ to $C_{10}$ alcohols such as methanol, ethanol, n propanol, i-propanol, n butanol, i butanol, t-butanol, pentanols, hexanols, ethylene glycol, propylene glycol, glycerol or a mixture of these. Methanol is preferred. Small amounts of esters, ethers, alkenes, aromatics, or other solvents can also be present.

The metal compounds dissolved in the polar organic solvent can conveniently be salts such as nitrates, sulfates, halides, phosphates, acetates, other carboxylates or the like. Nitrates are preferred.

The precipitating agent can be a base such as an alkali or alkaline earth metal or ammonium hydroxide, carbonate or bicarbonate or mixture thereof.

The temperature at which the precipitation is effected can vary widely but is conveniently from 10° to about 40° C. The order of addition is not critical.

The calcination is effected to decompose any thermally decomposable compounds especially salts to form the oxide and comprises heating in air to, for example, 250° to 750° C., preferably 300° to 450° C. for a sufficient period of time to decompose the compounds and form the oxides. Usually the duration of the calcination is from 1 to 6 hours.

Where an anion or anions other than oxide remains in the calcined solids then the calcined solids are treated to remove the anion prior to the use of the catalyst since the presence of anions tends to reduce the activity of the catalyst. The nature of the anion will depend on the metal salts from which the catalyst was precipitated since the source of the anion is the counterion of the metal in the salt used and may be, for example, chloride, nitrate, acetate or phosphate and the like.

The removal of these ions for example chloride, nitrate, acetate and phosphate is conveniently effected by washing with water or other suitable solvent.

Alternatively, the anions may, in suitable cases, be removed by gentle reduction, for example, nitrate and acetate can be removed by gently heating in a stream of a reducing gas such as carbon monoxide or hydrogen.

The washed catalyst can then be impregnated with an aqueous solution of an alkali or alkaline earth metal ions for example, lithium, sodium, potassium, rubidium, cesium, beryllium, magnesium, calcium, strontium or barium to increase the loading of metal A. Suitable compounds for dissolving in water to effect the impregnation are hydroxides, carbonates or bicarbonates. Conveniently up to 10 percent by weight of additional metal A may be added by impregnation.

Preferably the catalyst is formed into pellets by incorporation of a binding agent and pressing in a pellet press. Suitable binding agents include graphite, titanium dioxide, thorium dioxide, alumina, or zirconium dioxide. These agents may be used as a colloidal dispersion. Conveniently 1 to 10 percent, preferably 3 to 5 percent of graphite is useful as a binding agent.

The catalyst can be subjected to a reductive activation treatment before use by contacting with a suitable reducing gas such as hydrogen at a temperature suitable for at least partial reduction of one or more of the metal oxides to a reduced form. Conveniently a dilute stream of hydrogen in nitrogen (15 percent $H_2$, 85 percent $N_2$) is used and the catalyst is charged to a stainless steel tube placed in a programmable furnace capable of slowly raising the temperature from ambient to the highest temperature of the reduction, preferably 250° C. or the temperature at which the catalyst will be used in the subsequent reaction to form alcohols. The reduction is preferably accomplished at about atmospheric pressure although elevated pressures up to about 100 atmospheres can be used.

The feed and process conditions for the production of alcohols are as follows. Although synthesis gas is a preferred reactant, any other gas composed primarily of hydrogen and carbon monoxide and having an $H_2$ to CO ratio of about 1:10 to about 10:1, preferably about 1:3 to about 3:1, can be employed. The gaseous reactants should contain as little sulfur compounds as possible since sulfur is a known poison for copper containing catalysts. Preferably, the gaseous reactants are essentially sulfur-free.

The contact time of the reactants with the catalyst is not critical but should be below about 200 seconds and preferably between about 5 and 100 seconds.

The reaction pressure should normally be in the range of about 150 to about 4000 psig, preferably about 750 to about 1000 psig. Although there is no real upper limit to the reaction pressure, pressures higher than about 1500 psig or 2000 psig are normally not employed because of the high expense involved. It is preferable to operate at at least about 500 psig because formation of alcohols is favored at higher pressures.

The reaction temperature should be maintained in the range of about 100° to about 500° C., preferably about 220° to about 400° C., and more preferably about 250° to about 325° C.

The space velocity of the gaseous reactant is not critical but should be about 1000 to about 100,000, preferably about 2000 to about 20,000 liters of gaseous reactant per liter of catalyst per hour.

The process of the present invention yields alcohol compositions containing methanol and significant amounts of higher alcohols usually having 2 to about 8, preferably 2 to about 6 carbon atoms suitable for addition to gasoline. Normally, the alcohol compositions contain at least 30 percent by weight of methanol, although higher amounts of methanol may be included in the product if reaction temperature is too low or if the catalyst contains additional elements fostering the generation of higher amounts of methanol than normal.

The portion of the alcohol product other than methanol is usually a mixture composed primarily of 2 to about 6 carbon atom alcohols. The distribution of $C_2$–$C_6$ alcohols on a methanol-free basis is usually:

$C_2$—about 10 to about 90 percent,
$C_3$—about 15 to about 60 percent, preferably about 25 to about 55 percent,
$C_4$—about 0.5 to about 35 percent, preferably about 8 to about 30 percent,
$C_5$—about 0 to about 15 percent,
$C_6$—about 0 to about 15 percent.

Preferred compositions are those containing
$C_2$—10 to 25 percent,
$C_3$—40 to 60 percent,
$C_4$—10 to 25 percent,
$C_5$—5 to 15 percent,
$C_6$—0 to 5 percent, and,
$C_2$—40 to 70 percent,
$C_3$—25 to 45 percent,
$C_4$—5 to 15 percent,
$C_5$—0 to 10 percent,
$C_6$—0 to 5 percent.

The above-indicated percentages are by weight and based on the weight of the total amount of alcohols in the product having two or more carbon atoms. These alcohols are composed almost completely of isoalcohols and normal alcohols with the iso to normal ratio being in the range of about 0.01 to about 20. Preferably, substantially no tertiary alcohols are present.

The product alcohol mixtures of the present invention are useful in expanding gasoline. They can be mixed with gasoline in amounts up to about 25 percent by weight of the gasoline/alcohol mixture. Furthermore, the mixed alcohol products of the present invention can be mixed with any type of gasoline be it substantially all paraffinic such as alkylate or highly aromatic. Moreover, if the product alcohol mixtures employed have no more than about 85 percent by weight methanol, the resultant gasoline/alcohol mixture can tolerate significant amounts of water without phase separation.

Preferably, the alcohol mixtures produced in accordance with this invention contain not more than about 85 percent methanol, although those containing in excess of this figure for example up to about 95 percent methanol or more, can be used for addition with gasoline if such mixtures are blended with higher alcohols to provide a mixture with an overall methanol level of about 85 percent or less. These alcohol mixtures can be distilled to remove a sufficient amount of methanol to provide a mixture with a methanol level of about 85 percent or less.

The invention is illustrated by the following example in which all parts and percentages are by weight and all temperatures are in degrees centigrade unless otherwise indicated.

SPECIFIC EMBODIMENTS

Preparation 1—Preparation of Catalyst

The weights of reactants were chosen to correspond to a formula $Cu_{0.75}UAl_{0.3}K_xO_y$.

(a) 50 g of $Cu(NO_3)_2.2\frac{1}{2}H_2O$; 144 g of $U(NO_3)_2O_2.6H_2O$ and 32 g of $Al(NO_3)_3.9H_2O$ were dissolved in 2 liters of methanol. A 2 molar solution of potassium hydroxide in methanol was added to the mixture over a period of about one hour until the pH was 9.5 A 2 molar nitric acid solution was then added to the mixture until the pH was 7.0. The mixture was then vacuum filtered and the filter cake reslurried with 300 ml of methanol and vacuum filtered again. This was repeated until the filter cake had been washed three times. The filter cake was then placed in an oven at room temperature and slowly heated to 400° C. and this temperature maintained for two hours.

The thus prepared catalyst contained 6.2 percent copper, 30 percent uranium, 1.0 percent aluminum and 25 percent potassium all percentages being by weight based on the total weight of catalyst. The surface area was 0.41 $m^2$/g.

(b) Impregnation with Potassium

The catalyst was impregnated with more potassium and formed into pellets as follows: the catalyst was placed in a stainless steel beaker with about one liter of water and stirred vigorously for 1½ days. The solid material after that time was a fine powder which was then vacuum filtered through a medium glass frit and additionally washed with three 100 ml portions of distilled water while still on the frit. The solid was then dried in an oven at 110° C. overnight and then impregnated with an aqueous potassium hydroxide solution made by dissolving 1.91 g of 85 percent potassium hydroxide in enough water to make 18 ml of total solution volume. The weight of catalyst was 36.46 g. Following impregnation the catalyst was redried, then pelletized with 3 percent by weight of graphite and sieved to a 10–30 mesh fraction.

The finished catalyst contained
9.9 percent copper,
53 percent uranium,
2.6 percent aluminum,
8.2 potassium,
all percent being by weight of the catalyst corresponding to a formula. The surface area was 27.1 $m^2$/g determined by nitrogen absorption.

The product was examined by x-ray diffraction and found to contain potassium uranate.

Preparation 2—Preparation of Catalyst

The weights of reactants were chosen to correspond to the formula $Cu_{0.75}UAl_{0.3}K_xO_y$.

50 g of $Cu(NO_3)_2.2\frac{1}{2}H_2O$ (0.215 mole of copper), 144 g of $UO_2(NO_3)_2.6H_2O$ (0.287 mole of uranium), and 32 g of $Al(NO_3)_3.9H_2O$ (0.0853 mole of aluminum) were dissolved in 2 liters of methanol at room temperature.

While vigorously stirring the solution, enough 2 molar potassium hydroxide in methanol was added by slow dropwise addition to bring the pH to 7.0. The precipitate was light green in color and was vacuum filtered, then washed once by reslurrying with two liters of absolute methanol and refiltering. The filter cake was then dried and calcined in one step by heating as follows: 25° C. to 400° C. at 1° C. per minute and then held at 400° C. for two hours and then allowed to cool to room temperature. The calcined solid, of mottled brown and yellow appearance was washed by stirring with one liter of distilled water for about 12 hours and was then vacuum filtered with a medium glass frit. The solid was washed a further three times while on the frit with 50 ml portions of distilled water and then dried overnight at 110° C. At this stage the material contained 11 percent copper, 56 percent uranium, 2.0 percent aluminum and 5.6 percent potassium. The surface area was 48.9 m²/g. The product was examined by x-ray diffraction and found to contain potassium uranate. This material was then impregnated with a further 3 percent by weight of potassium (as KOH) redried, then pelletized with 3 percent by weight of graphite. The finished catalyst contained 10 percent copper, 54 percent uranium, 1.8 percent aluminum, and 8.7 percent potassium all by weight of the catalyst. The surface area was 17.8 m²/g.

Preparation 3—Preparation of Catalyst

The weights of reactants were chosen to correspond to the formula $Cu_{0.75}UAlK_xO_y$.

70 g of the solid prepared in part (a) of Preparation 1 were stirred vigorously with 250 ml of water for one hour. The resulting slurry was vacuum filtered using a medium glass frit Buchner filter, then washed three more times with 25 ml portions of distilled water. The filter cake was dried in an oven overnight at 100° C. The dried filter cake contained 11 percent copper, 58 percent uranium, 2.0 percent aluminum and 7.3 percent potassium. The product was examined by x-ray diffraction and found to contain potassium uranate. The product was pelletized with 3 percent by weight of graphite, and the pellets broken up to yield a 10–30 mesh fraction.

In the following examples a 20.0 cc sample of the catalyst was loaded into a reactor and reduced by programmed heating under 1.8 SLPM of a 1:5 volume ratio of hydrogen and nitrogen to a final temperature of 250° C. The catalyst was allowed to cool and the reactor was pressured to the desired pressure with synthesis gas (composition indicated in example) and heated by a programmed heating procedure under a flow of the synthesis gas to the desired reaction temperature. The liquid products were collected and analyzed by gas chromotography. The results are summarized in Table 1.

TABLE 1

| Alcohol Distribution Obtained over Cu—U—Al—K Catalysts | | | | | |
|---|---|---|---|---|---|
| Example Number | Preparation Catalyst Number | H₂/CO Molar Ratio | Temp. °C. | Space Velocity Vol of Gas/ Vol Catalyst/ Hour | Weight Percent Methanol |
| 1 | 1 | 0.46 | 285 | 2400 | 77.9 |
| 2 | 1 | 0.46 | 300 | 2400 | 69.1 |
| 3 | 1 | 0.46 | 325 | 2400 | 45.7 |
| 4 | 1 | 1 | 285 | 2400 | 80.6 |
| 5 | 1 | 1 | 300 | 2400 | 73.3 |
| 6 | 1 | 1 | 325 | 2400 | 57.8 |
| 7 | 2 | 0.81 | 285 | 2400 | 81.7 |

TABLE 1-continued

| Alcohol Distribution Obtained over Cu—U—Al—K Catalysts | | | | | |
|---|---|---|---|---|---|
| Example Number | Preparation Catalyst Number | H₂/CO Molar Ratio | Temp. °C. | Space Velocity Vol of Gas/ Vol Catalyst/ Hour | Weight Percent Methanol |
| 8 | 2 | 0.81 | 300 | 2400 | 75.7 |
| 9 | 2 | 0.81 | 325 | 2400 | 59.3 |
| 10 | 3 | 1 | 285 | 2400 | 84.3 |
| 11 | 3 | 1 | 300 | 2400 | 72.8 |
| 12 | 3 | 1 | 325 | 2400 | 61.9 |
| 13 | 3 | 2 | 200 | 9000 | 82.7 |
| 14 | 3 | 2 | 220 | 9000 | 91.4 |
| 15 | 3 | 2 | 240 | 9000 | 91.2 |

Pressure 1000 psig

The weight percent of methanol is based on the total weight of liquid product. The weight percentages were determined by gas liquid chromatography. The amount of non-alcohol liquid products such as aldehydes, esters and ketones in no case exceeded 3 percent.

| Weight Percent on a Methanol-Free Basis** | | | | | | |
|---|---|---|---|---|---|---|
| Example Number | Weight Percent HA | $C_2/C_2+$ | $C_3/C_2+$ | $C_4/C_2+$ | $C_5/C_2+$ | $C_6/C_2+$ |
| 1 | 22.1 | 45.6 | 36.5 | 8.5 | 6.6 | 2.8 |
| 2 | 30.9 | 33.1 | 43.3 | 11.8 | 8.2 | 3.6 |
| 3 | 54.3 | 17.1 | 51.9 | 17.2 | 10.1 | 3.6 |
| 4 | 19.4 | 48.9 | 32.9 | 12.9 | 5.3 | 0.0 |
| 5 | 26.7 | 35.1 | 44.2 | 10.7 | 7.4 | 2.5 |
| 6 | 42.2 | 16.7 | 53.4 | 16.5 | 9.9 | 3.6 |
| 7 | 18.3 | 52.6 | 34.9 | 12.4 | 0.0 | 0.0 |
| 8 | 24.3 | 33.6 | 42.1 | 14.5 | 7.1 | 2.8 |
| 9 | 40.7 | 16.9 | 55.3 | 19.1 | 4.9 | 3.7 |
| 10 | 15.7 | 26.8 | 34.7 | 18.9 | 9.8 | 9.7 |
| 11 | 27.2 | 21.9 | 35.6 | 23.4 | 10.6 | 8.4 |
| 12 | 38.1 | 15.6 | 38.6 | 28.8 | 10.0 | 6.9 |
| 13 | 17.3 | 17.0 | 37.3 | 25.7 | 12.3 | 7.6 |
| 14 | 8.6 | 41.3 | 33.8 | 15.1 | 5.8 | 3.9 |
| 15 | 8.8 | 53.3 | 25.7 | 16.0 | 4.9 | 0.0 |

**Percent of the indicated carbon number alcohols as a fraction of all the higher alcohols, e.g. (Wt C₂OH × 100)/Wt C₂+ Alcohols.

The abbreviation HA stands for higher alcohols. This means alcohols containing two or more carbon atoms. The symbol C₂ means alcohols containing two carbon atoms. The symbol C₂+ means all alcohols containing two or more carbon atoms.

The above results show the alcohol compositions produced, in each case, contained at least 39 percent by weight of methanol and that the ratio of C₃ to C₄ alcohols was at least 1.25.

Alcohol/Gasoline Composition

The alcohol mixture of Example 4 was mixed with motor gasoline in a weight ratio of 10:90 and a clear homogeneous solution was obtained.

Preparation 8—Preparation of Catalyst

The proportions of the reactants employed were chosen to correspond to a catalyst of the formula:

$Cu_{1.5}UAl_{0.2}K_xO_y$ 100 g of $Cu(NO_3)_2.2\frac{1}{2}H_2O$, 144 g of $UO_2(NO_3)_2.6-H_2O$ and 22.0 g of $Al(NO_3)_3.9H_2O$ were dissolved in two liters of methanol. A two molar KOH in methanol solution was then added to the mixture over a period of one hour and 15 minutes until the pH was 7.0. The mixture was then vacuum filtered and the filter cake placed in a room temperature oven and slowly heated to 400° C. and calcined at that temperature for two hours. After cooling to room temperature the catalyst was then ground to a powder and dispersed in one liter of distilled water. The catalyst mixture was then vacuum filtered and the filter cake reslurried with one liter of distilled water and again vacuum filtered. The catalyst was then placed in an oven at 120° C. and dried over night. The catalyst was split into four portions. One portion was designated 8A. Catalyst 8A had the following analysis:

Cu 19 percent,
U 51 percent,
Al 1.2 percent,
K 8.4 percent, corresponding to a formula of $Cu_{1.4}UAl_{0.2}K_{1.0}$. Another portion was doped by adding a solution of KOH in distilled water until an additional 3 percent potassium K+ was added. The doped catalyst was then dried in an oven at 120° C. The catalyst was pelletized with 3 percent graphite and designated 8B. Catalyst 8B had the following analysis:

Cu 17 percent,
U 47 percent,
Al 1.1 percent,
K 10.0 percent, corresponding to a formula of $Cu_{1.4}UAl_{0.2}K_{1.3}$. A second portion of catalyst was doped by adding a solution of NaOH in distilled water until the added sodium level reached 1.5 percent. The doped catalyst was then dried in an oven at 120° C. and pelletized with 3 percent graphite and designated 8C. Catalyst 8C had the following analysis:

Cu 17 percent,
U 46 percent,
Al 1.1 percent,
K 7.6 percent,
Na 1.4 percent, corresponding to a formula of $Cu_{1.4}UAl_{0.2}K_{1.0}Na_{0.3}$. Another portion of the catalyst was doped by adding a solution of CsOH in distilled water until the cesium level reached 9 percent. The doped catalyst was then dried in an oven at 120° C., pelletized with 3 percent graphite and designated 8D. Catalyst 8D had the following analysis:

Cu 16 percent,
U 42 percent,
Al 0.97 percent,
K 6.7 percent,
Cs 8.3 percent, corresponding to a formula of $Cu_{1.4}UAl_{0.2}K_{1.0}Cs_{0.4}$.

Preparation 9 Catalyst Preparation

The proportions of the reactants employed were chosen to correspond to a formula of $Cu_{1.5}UAl_{0.2}Ba_x O_yK_z$ 50.0 g of $Cu(NO_3)_2 \cdot 2\frac{1}{2}H_2O$, 72.26 g of $UO_2(NO_3)_2 \cdot 6H_2O$ and 10.80 g of $Al(NO_3)_3 \cdot 9H_2O$ were dissolved in one liter of methanol. 14.21 g of $BaCO_3$ was then added to the solution. A 2M solution of KOH in methanol was then added over a period of about one hour and 30 minutes until the pH was 9.90. The mixture was then vacuum filtered, the filtercake reslurried with one liter of methanol and vacuum filtered again. The solid was then placed in a room temperature furnace and slowly heated to 350° C. and calcined at that temperature for two hours and cooled to room temperature.

The solid was ground to a powder and dispersed in one liter of distilled water. The solid was then vacuum filtered and the filtercake dried in an oven at 120° C. The finished material was designated Catalyst 10.

Analysis of Catalyst 10 was:
Cu 18 percent,
U 48 percent,
Al 1.0 percent,
K 4.5 percent,
Ba 6.7 percent, corresponding to a formula of: $Cu_{1.4}UAl_{0.18}K_{0.57}Ba_{0.24}$. This Preparation shows that the atomic proportions of Cu and U are close to the formula calculated from the weights of salts dissolved.

X-ray diffraction data for the catalysts prepared as described above is summarized in Table A.

The catalysts prepared in Preparations 8 and 9 were tested for activity and the results are summarized in Tables 2-4.

TABLE A

X-Ray Diffraction Data for Cu—U Catalysts

| Compound | | 8A | 8B | 8C | 8D | 9 |
|---|---|---|---|---|---|---|
| 7.01 A | K2 U4 013 | na | na | 0 | 0 | 66 |
| 6.60 A | K2 U2 07 | na | na | 135 | 130 | 16 |
| 3.78 A | K N03 | 0 | 0 | 0 | 0 | 0 |
| 3.48 A | K2U4013/CuU04 | 45 | 45 | 45 | 43 | 100 |
| 3.37 A | Graphite | 10 | 110 | 105 | 80 | 0 |
| 3.28 A | K2U207/CuU3010 | 100 | 100 | 100 | 100 | 15 |
| 3.12 A | K2U4013 | 10 | 5 | 15 | 5 | 85 |
| 2.85 A | K2U207/CuU04 | 15 | 15 | 20 | 20 | 0 |
| 2.62 A | K2U207 | 3 | 3 | 2 | 5 | 5 |
| 2.53 A | CuO | 12 | 12 | 12 | 15 | 10 |
| 2.33 A | CuO | 15 | 13 | 15 | 15 | 18 |
| 2.19 A | K2U207 | 10 | 12 | 12 | 14 | 0 |
| 2.02 A | K2U207 | 20 | 25 | 25 | 30 | 21 |
| 1.92 A | K2U207/CuU04/CuU3010 | 12 | 8 | 12 | 15 | 25 |
| 1.87 A | CuO | 2 | 2 | 2 | 2 | 15 |

The figures in the Table show the relative intensities of the x-ray lines. The strong lines at 6.60 A and 7.01 A show the presence of significant amounts of (i) $K_2U_2O_7$ in Catalysts 8C and 8D and (ii) the presence of $K_2U_4O_{13}$ in Catalyst 9 respectively.

Since all the Catalysts 8A, 8B, 8C and 8D were prepared by the same technique (apart from the impregnation) it is concluded that they all contain potassium uranates.

TABLE 2

| | Example No. | 16 | 17 | 18 | 19 | 20 | 21 |
|---|---|---|---|---|---|---|---|
| 1 | Cat. No. | 8C | 8C | 8C | 8D | 8D | 8D |
| 2 | Hydrogen/Carbon Monoxide Molar Ratio | 1 | 1 | 1 | 1 | 1 | 1 |
| 3 | Temp. °C. | 285 | 300 | 325 | 285 | 300 | 325 |
| 4 | Press psig | 1000 | 1000 | 1000 | 1000 | 1000 | 1000 |
| 5 | SV h-1 | 4800 | 4800 | 4800 | 4800 | 4800 | 4800 |
| | Analysis of Product Weight Percent | | | | | | |
| 6 | ClOH | 83.2 | 75.6 | 66.9 | 81.3 | 72.7 | 75.3 |
| 7 | C2+ Alcs. | 16.8 | 24.4 | 33.1 | 18.7 | 27.3 | 24.7 |
| | Methanol-Free Basis | | | | | | |
| 8 | C2/C2+ | 46.1 | 34.9 | 21.9 | 40.1 | 32.9 | 24.6 |
| 9 | C3/C2+ | 28.3 | 35.5 | 50.5 | 42.2 | 39.4 | 37.8 |
| 10 | C4/C2+ | 17.7 | 17.7 | 21.9 | 15.6 | 20.2 | 21.2 |
| 11 | C5/C2+ | 6.6 | 8.5 | 1.9 | 2.1 | 2.5 | 8.8 |
| 12 | C6/C2+ | 1.4 | 3.3 | 3.9 | 0.0 | 4.9 | 7.7 |

TABLE 3

| Example No. | 22 | 23 | 24 | 25 | 26 | 27 |
|---|---|---|---|---|---|---|
| 1 Cat. No. | 8B | 8B | 8B | 9 | 9 | 9 |
| 2 Hydrogen/Carbon Monoxide Molar Ratio | 1 | 1 | 1 | 2 | 2 | 2 |
| 3 Temp. °C. | 285 | 300 | 325 | 240 | 260 | 260 |
| 4 Press psig | 1000 | 1000 | 1000 | 1000 | 1000 | 1000 |
| 5 SV h-1 | 4800 | 4800 | 4800 | 9000 | 9000 | 36000 |
| Analysis of Product Weight Percent | | | | | | |
| 6 C1OH | 83.1 | 72.2 | 61.1 | 93.8 | 93.1 | 95.2 |
| 7 C2 + Alcs. | 16.9 | 27.8 | 38.9 | 6.2 | 6.9 | 4.8 |
| Methanol-Free Basis | | | | | | |
| 8 C2/C2+ | 47.7 | 36.9 | 18.6 | 79.4 | 69.5 | 73.1 |
| 9 C3/C2+ | 27.2 | 40.2 | 46.4 | 16.6 | 20.6 | 19.9 |
| 10 C4/C2+ | 16.2 | 17.1 | 20.8 | 2.9 | 7.2 | 5.6 |
| 11 C5/C2+ | 6.6 | 2.1 | 10.3 | 1.0 | 2.6 | 1.5 |
| 12 C6/C2+ | 2.3 | 3.7 | 3.9 | 0.0 | 0.0 | 0.0 |

TABLE 4

| Example No. | 28 | 29 |
|---|---|---|
| 1 Cat. No. | 8D | 8D |
| 2 Hydrogen/Carbon Monoxide Molar Ratio | 2 | 2 |
| 3 Temp. °C. | 260 | 280 |
| 4 Press psig | 1000 | 1000 |
| 5 SV h-1 | 18857 | 18857 |
| Analysis of Product In Percent by Weight | | |
| 6 C1OH | 95.4 | 94.3 |
| 7 C2+ Alcohols | 4.6 | 5.7 |
| Methanol-Free Basis | | |
| 8 C2/C2+ | 80.4 | 71.0 |
| 9 C3/C2+ | 18.6 | 22.1 |
| 10 C4/C2+ | 0.9 | 5.1 |
| 11 C5/C2+ | 0.0 | 1.8 |
| 12 C6/C2+ | 0.0 | 0.0 |

In Tables 2–4:

The abbreviation "SV" stands for Space Velocity and is measured in volumes of gas per volume of catalyst per hour. The symbol "ClOH" means methanol.

The results in Tables 2–3 show that the products of the examples in each case contain at least 39 percent of methanol and that the ratio of $C_3$ to $C_4$ is greater than 1.25:1.

We claim:

1. An alcohol composition suitable for mixing with gasoline comprising at least 30 percent by weight of methanal, the remainder of said composition comprising higher alcohols the distribution of which on a methanol-free basis is $C_2$—about 10 to 90 weight percent,
   $C_3$—greater than 25 to 60 weight percent,
   $C_4$—about 0.5 to 35 weight percent, and wherein the percent of $C_3$ is equal to or greater than 1.25 times the percent of $C_4$ and wherein the alcohol composition is prepared by a process which comprises contacting carbon monoxide and hydrogen under alcohol forming conditions at elevated temperature and pressure with a catalyst composition containing alkali or alkaline earth metal uranate of the formula $Cu_aUAl_bA_cO_x$ where A is an alkali or alkaline earth metal;
   a is from 0.01 to 5.0;
   b is a number up to 5.0;
   c is a number up to 5.0 selected so that the catalyst contains more than 2 percent by weight of metal A;
   x is a number such that the valence requirements of the other elements for oxygen are satisfied.

2. The alcohol composition as claimed in claim 1 wherein said mixture contains no more than about 95 weight percent methanol.

3. The alcohol composition as claimed in claim 2 wherein said mixture contains no more than about 85 weight percent methanol.

4. The alcohol composition as claimed in claim 1 wherein said mixture contains $C_2$—about 10 to 25 weight percent,
   $C_3$—about 40 to 60 weight percent,
   $C_4$—about 10 to 25 weight percent,
   $C_5$—about 5 to 15 weight percent,
   $C_6$—about 0 to 5 weight percent.

5. The alcohol composition as claimed in claim 1 wherein said mixture contains $C_2$—about 40 to 70 weight percent,
   $C_3$—about 25 to 45 weight percent,
   $C_4$—about 5 to 15 weight percent,
   $C_5$—about 0 to 10 weight percent,
   $C_6$—about 0 to 5 weight percent.

6. The alcohol composition as claimed in claim 1 wherein $C_3$ alcohols are present in an amount of 25 to 55 weight percent and $C_4$ alcohols are present in an amount of 8 to 30 weight percent.

7. A modified gasoline composition containing a homogeneous solution of gasoline and a composition of alcohols wherein said composition of alcohols comprises at least about 30 percent by weight methanol, the remainder of said composition comprising higher alcohols, the distribution of said higher alcohols on a methanol-free basis being $C_2$—about 10 to 90 weight percent,
   $C_3$—about 15 to 60 weight percent,
   $C_4$—about 0.5 to 35 weight percent,
   $C_5$—about 0 to 15 weight percent,
   $C_6$—about 0 to 15 weight percent.

8. The modified gasoline composition as claimed in claim 7 wherein said alcohol composition contains no more than 85 weight percent methanol.

9. The gasoline composition as claimed in claim 8 wherein $C_3$ alcohols are present in an amount of 25 to 55 weight percent and $C_4$ alcohols are present in an amount of 8 to 30 weight percent.

10. The gasoline composition as claimed in claim 7 wherein the gasoline component of said modified gasoline contains both paraffinic and aromatic fractions.

11. The gasoline composition as claimed in claim 7 wherein the gasoline component of said modified gasoline contains paraffins only.

12. The alcohol composition as claimed in claim 1 which contains at least 0.1 percent of $C_5$ and 0.1 percent of $C_6$ alcohols on a methanol-free basis.

13. The alcohol composition as claimed in claim 12 wherein $C_3$ alcohols are present in an amount of 25 to 55 weight percent and $C_4$ alcohols are present in an amount of 8 to 30 weight percent.

14. The alcohol compositon as claimed in claim 1 wherein $C_3$ alcohols are present in amount from 25.7 to 60 weight percent.

* * * * *